(12) United States Patent
Bille

(10) Patent No.: US 8,646,916 B2
(45) Date of Patent: Feb. 11, 2014

(54) SYSTEM FOR CHARACTERIZING A CORNEA AND OBTAINING AN OPTHALMIC LENS

(75) Inventor: Josef F. Bille, Heidelberg (DE)

(73) Assignee: Perfect IP, LLC, Dallas, TX (US)

( * ) Notice: Subject to any disclaimer, the term of this patent is extended or adjusted under 35 U.S.C. 154(b) by 0 days.

(21) Appl. No.: 12/717,866

(22) Filed: Mar. 4, 2010

(65) Prior Publication Data

US 2010/0225014 A1    Sep. 9, 2010

Related U.S. Application Data

(60) Provisional application No. 61/209,362, filed on Mar. 4, 2009, provisional application No. 61/209,363, filed on Mar. 4, 2009, provisional application No. 61/181,420, filed on May 27, 2009, provisional application No. 61/181,519, filed on May 27, 2009, provisional application No. 61/181,525, filed on May 27, 2009.

(51) Int. Cl.
  *A61B 3/107* (2006.01)
  *B29D 11/00* (2006.01)

(52) U.S. Cl.
  USPC .................... 351/246; 264/1.37; 351/212

(58) Field of Classification Search
  USPC ............ 356/601, 625, 628, 629; 264/1.37; 250/307; 351/200, 205, 211, 212, 246; 606/5
  See application file for complete search history.

(56) References Cited

U.S. PATENT DOCUMENTS

| | | | |
|---|---|---|---|
| 4,579,430 A | 4/1986 | Bille | |
| 4,787,903 A | 11/1988 | Grendahl | |
| 5,050,981 A | 9/1991 | Roffman | |
| 5,178,636 A | 1/1993 | Silberman | |
| 5,394,199 A | 2/1995 | Flower | |
| 5,589,982 A | 12/1996 | Faklis | |
| 6,050,687 A * | 4/2000 | Bille et al. | 351/212 |

(Continued)

FOREIGN PATENT DOCUMENTS

| | | |
|---|---|---|
| WO | WO00/41650 A1 | 7/2000 |
| WO | WO01/08547 A2 | 2/2001 |

(Continued)

OTHER PUBLICATIONS

Wikipedia, "Two-photon excitation microscopy".

(Continued)

*Primary Examiner* — Mathieu D. Vargot
(74) *Attorney, Agent, or Firm* — David W. Carstens; Jeffrey G. Degenfelder; Carstens & Cahoon, LLP

(57) ABSTRACT

A system for determining the shape of a cornea of an eye illuminates at least one of the interior surface, the posterior surface, and the interior region of the eye with infrared light of a wavelength that can generate fluorescent light from the portion of the cornea illuminated. The generated fluorescent light is then detected. A step of illuminating can comprise focusing the infrared light in a plurality of different planes substantially perpendicular to the optical axis of the eye. From the detected light it is possible to create a map of at least a portion of the interior surface, at least a portion of the posterior surface, and/or portion of the interior region of the cornea. Clarity of vision can be determined by generating autofluorescence from proteins in the pigment epithelial cells of the retina.

9 Claims, 11 Drawing Sheets

(56) References Cited

U.S. PATENT DOCUMENTS

| | | |
|---|---|---|
| 6,155,684 A | 12/2000 | Bille et al. |
| 6,220,707 B1 | 4/2001 | Bille |
| 6,361,170 B1 | 3/2002 | Bille |
| 6,399,734 B1 | 6/2002 | Hodd |
| 6,413,276 B1 | 7/2002 | Werblin |
| 6,443,984 B1 | 9/2002 | Jahn |
| 6,464,725 B2 | 10/2002 | Skotton |
| 6,499,843 B1 | 12/2002 | Cox et al. |
| 6,511,180 B2 | 1/2003 | Guirao |
| 6,536,898 B1 | 3/2003 | Cathey, Jr. |
| 6,585,375 B2 | 7/2003 | Donitzky |
| 6,613,041 B1* | 9/2003 | Schrunder ............ 606/5 |
| 6,626,535 B2 | 9/2003 | Altmann |
| 6,663,240 B2 | 12/2003 | Patel |
| 6,730,123 B1 | 5/2004 | Klopotek |
| 6,762,271 B2 | 7/2004 | Salamone et al. |
| 6,770,728 B2 | 8/2004 | Watanabe et al. |
| 6,777,522 B2 | 8/2004 | Lai et al. |
| 6,813,097 B2 | 11/2004 | Jethmalani et al. |
| 6,817,714 B2 | 11/2004 | Altmann |
| 6,824,266 B2 | 11/2004 | Jethmalani et al. |
| 6,836,374 B2 | 12/2004 | Esch |
| 6,848,790 B1 | 2/2005 | Dick et al. |
| 6,849,671 B2 | 2/2005 | Steffen et al. |
| 6,851,804 B2 | 2/2005 | Jethmalani |
| 6,858,218 B2 | 2/2005 | Lai |
| 6,860,601 B2 | 3/2005 | Shadduck |
| 6,881,809 B2 | 4/2005 | Salamone et al. |
| 6,905,641 B2 | 6/2005 | Platt et al. |
| 6,908,978 B2 | 6/2005 | Salamone et al. |
| 6,935,743 B2 | 8/2005 | Shadduck |
| 6,951,914 B2 | 10/2005 | Lai |
| 6,966,649 B2 | 11/2005 | Shadduck |
| 7,001,374 B2 | 2/2006 | Peyman |
| 7,005,494 B2 | 2/2006 | Salamone et al. |
| 7,022,749 B2 | 4/2006 | Salamone et al. |
| 7,025,454 B2 | 4/2006 | Cathey, Jr. |
| 7,033,391 B2 | 4/2006 | Lai |
| 7,037,954 B2 | 5/2006 | Baba et al. |
| 7,061,693 B2 | 6/2006 | Zalevsky |
| 7,068,439 B2 | 6/2006 | Esch et al. |
| 7,074,840 B2 | 7/2006 | Chang et al. |
| 7,104,648 B2 | 9/2006 | Dahi et al. |
| 7,105,110 B2 | 9/2006 | Platt et al. |
| 7,118,214 B2 | 10/2006 | Cox |
| 7,134,755 B2 | 11/2006 | Jethmalani et al. |
| 7,163,292 B2 | 1/2007 | Dahi et al. |
| 7,210,783 B2 | 5/2007 | Jethmalani et al. |
| 7,237,893 B2 | 7/2007 | Chang et al. |
| 7,241,311 B2 | 7/2007 | Norrby et al. |
| 7,281,795 B2 | 10/2007 | Sandstedt et al. |
| 7,377,645 B2 | 5/2008 | Wrobel et al. |
| 7,438,723 B2 | 10/2008 | Esch |
| 7,478,907 B2 | 1/2009 | Somani |
| 7,510,283 B2 | 3/2009 | Bille |
| 7,611,244 B2 | 11/2009 | Bille |
| 7,703,923 B2 | 4/2010 | Bille |
| 2002/0016629 A1 | 2/2002 | Sandstedt et al. |
| 2002/0026181 A1 | 2/2002 | O'Donnell, Jr. |
| 2002/0100990 A1 | 8/2002 | Platt et al. |
| 2002/0133228 A1 | 9/2002 | Sarver |
| 2002/0154271 A1 | 10/2002 | Donitzky et al. |
| 2003/0090013 A1 | 5/2003 | Jethmalani et al. |
| 2003/0090624 A1 | 5/2003 | Jethmalani et al. |
| 2003/0128336 A1 | 7/2003 | Jethmalani et al. |
| 2003/0151719 A1 | 8/2003 | Jethmalani et al. |
| 2003/0171808 A1 | 9/2003 | Phillips |
| 2003/0171809 A1 | 9/2003 | Phillips |
| 2003/0173691 A1 | 9/2003 | Jethmalani et al. |
| 2003/0187503 A1 | 10/2003 | Lipshitz et al. |
| 2004/0010310 A1 | 1/2004 | Peyman |
| 2004/0073304 A1 | 4/2004 | Weinschenk, III et al. |
| 2004/0169932 A1 | 9/2004 | Esch et al. |
| 2004/0249454 A1 | 12/2004 | Terwee |
| 2005/0113911 A1 | 5/2005 | Peyman |
| 2005/0149183 A1 | 7/2005 | Shadduck |
| 2005/0159733 A1 | 7/2005 | Dick et al. |
| 2005/0182489 A1 | 8/2005 | Peyman |
| 2005/0187622 A1 | 8/2005 | Sandstedt et al. |
| 2005/0273163 A1 | 12/2005 | Tran et al. |
| 2006/0084949 A1 | 4/2006 | Peyman |
| 2006/0087614 A1 | 4/2006 | Shadduck |
| 2006/0155372 A1 | 7/2006 | Coroneo |
| 2006/0216329 A1 | 9/2006 | Peyman |
| 2006/0259138 A1 | 11/2006 | Peyman |
| 2006/0261502 A1 | 11/2006 | Plat et al. |
| 2007/0035698 A1 | 2/2007 | Jethmalani et al. |
| 2007/0103642 A1 | 5/2007 | Bille |
| 2007/0129802 A1 | 6/2007 | Jethmalani et al. |
| 2007/0213618 A1* | 9/2007 | Li et al. ............ 600/476 |
| 2007/0299487 A1 | 12/2007 | Shadduck |
| 2008/0001320 A1 | 1/2008 | Knox et al. |
| 2008/0015448 A1* | 1/2008 | Keely et al. ............ 600/477 |
| 2008/0027537 A1 | 1/2008 | Gerlach et al. |
| 2008/0073525 A1* | 3/2008 | Gross et al. ............ 250/307 |
| 2008/0086207 A1 | 4/2008 | Sandstedt et al. |
| 2008/0252845 A1 | 10/2008 | Dreher et al. |
| 2008/0269731 A1 | 10/2008 | Swinger et al. |
| 2009/0000628 A1 | 1/2009 | Somani et al. |
| 2009/0005764 A1 | 1/2009 | Knox et al. |
| 2009/0271155 A1* | 10/2009 | Dupps et al. ............ 703/1 |

FOREIGN PATENT DOCUMENTS

| | | |
|---|---|---|
| WO | WO02/45578 A1 | 6/2002 |
| WO | WO02/051338 A1 | 7/2002 |
| WO | WO2007/120755 A1 | 10/2007 |
| WO | WO2008/002796 A2 | 1/2008 |

OTHER PUBLICATIONS

Richardson, M., "Ablation and optical property modification of transparent materials with femtosecond lasers" Proceedings of SPIE, 2003, vol. 5273 pp. 472-481.

Gattass, Rafael, "Micromachining of bulk glass with bursts of femtosecond laser pulses at variable repetition rates" Optics Express Jun. 2006, vol. 14, No. 12, pp. 5279-5284.

Schaffer, Crhis B., "Micromachining bulk glass by use of femtosecond laser pulses with nanojoule energy", Optical Society of America, Jan. 15, 2001, vol. 26, No. 2, pp. 93-95.

Schwartz, Daniel M., MD, "Post implantation adjustable intraocular lenses", Ophthalmology Clinics of North America, vol. 14, Issue 2, Jun. 2001, 8 pages, Saunders Company.

Sowa, Seiji, "Symmetric waveguides in poly(methyl methacrylate) fabricated by femtosecond laser pulses", Optics Express, Jan. 9, 2006, vol. 14, No. 1, pp. 291-297.

Mendonca, C.R., "Reversible birefringence in microstructures fabricated by two-photon absorption polymerization", Hournal of Applied Physics 102, 013109 (2007), pgs.

Ashcom, Jonathan B., "Numerical aperture dependence of damage and supercontinuum generation from femtosecond laser pulses inbulk fused silica", J. Opt. Soc. Am. B. vol. 23, No. 11, pp. 2317-2322.

Borrelli, N.F., "Infrared photosensitivity in silica glasses exposed to femtosecond laser pulses", Optics Letters, Sep. 15, 1999, vol. 24, No. 18, pp. 1311-1313.

Treacy, Edmond, "Optical Pulse Compression with Diffraction Gratings", IEEE Journal of quantum Electronics, vol. QE-5, No. 9, Sep. 1969.

Fork, R.I., "Negative dispersion using pairs of prisms", Optics Letters vol. 9, No. 5, May 1984, pp. 150-152.

Mailis, Sakellaris, "Photosensitivity of lead germanate glass waveguides grown by pulsed laser deposition", Optics Letters, Nov. 15, 1998, vol. 23, No. 22, pp. 1751-1753.

Muller, M., "Dispersion pre-compensation of 15 femtosecond optical pulses for high-numerical-aperture objectives", Journal of Microscopy, vol. 191, Pt. 2, Aug. 1998, pp. 141-150.

(56) References Cited

OTHER PUBLICATIONS

HRT Rostock Cornea Module, Heidelberg Engineering, http://www.heidelbergengineering.com/products/cornea-module.

"Quantitative Three-Dimensional Imaging of the Posterior Segment with the Heidelberg Retina Tomograph", pp. 1-16. Heidelberg Engineering GmbH, Heidelberg, Germany.

Han, Meng, "Second harmonic generation imaging of collagen fibrils in cornea and sclera", Optics Express Jul. 25, 2005, vol. 13, No. 15 pp. 5791-5797.

Pandolfi, A., "A model for the human cornea: constitutive formulation and numerical analysis", Biomechan Model Mechanobiol 2006 5:237-246.

Gattass, Rafael R., "Femtosecond laser micromachining in transparent materials", Nature photonics vol. 2, Apr. 2008, pp. 219-225.

Scully, P.J., "Femtosecond laser irradiation of polymethylmethacrylate for refractive index gratings", J. Opt. A: Pure Appl. Opt. 5 (2003) pp. S92-S96, IOP Publishing UK.

Richardson, M., "Femtosecond laser micro-structuring and refractive index modification applied to laser and photonic devices", Proc. of SPIE vol. 5347, 2004, pp. 18-27.

Zoubir, Arnaud, "Femtosecond laser fabrication of tubular waveguides in poly(methyl methacrylate)", Optics Letters, vol. 29, No. 16, Aug. 15, 2004, pp. 1840-1842.

International Search Report and Written Opinion, PCT/US2010/026281, Jul. 8, 2010.

Morishige et al., "Three-Dimensional Analysis of Collagen Lamellae in the Anterior Stroma of the Human Cornea Visualized by Second Harmonic Generation Imaging Microscopy", IOVS Papers in Press. Published on Sep. 29, 2010 as Manuscprit iovx. 10-5657.

Morishige et al., "Second-Harmonic Imaging Microscopy of Normal Human and Keratoconus Cornea, Investigative Ophthalmology & Visual Science", Mar. 2007, vol. 48, No. 3.

Teng et al. "Multiphoton Autofluorescence and Second-Harmonic Generataion Imaging of the Ex Vivo Porcine Eye", Investigative Ophthalmology & Visual Science, Mar. 2006, vol. 47, No. 3.

* cited by examiner

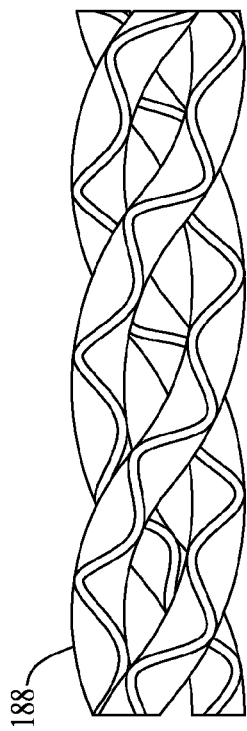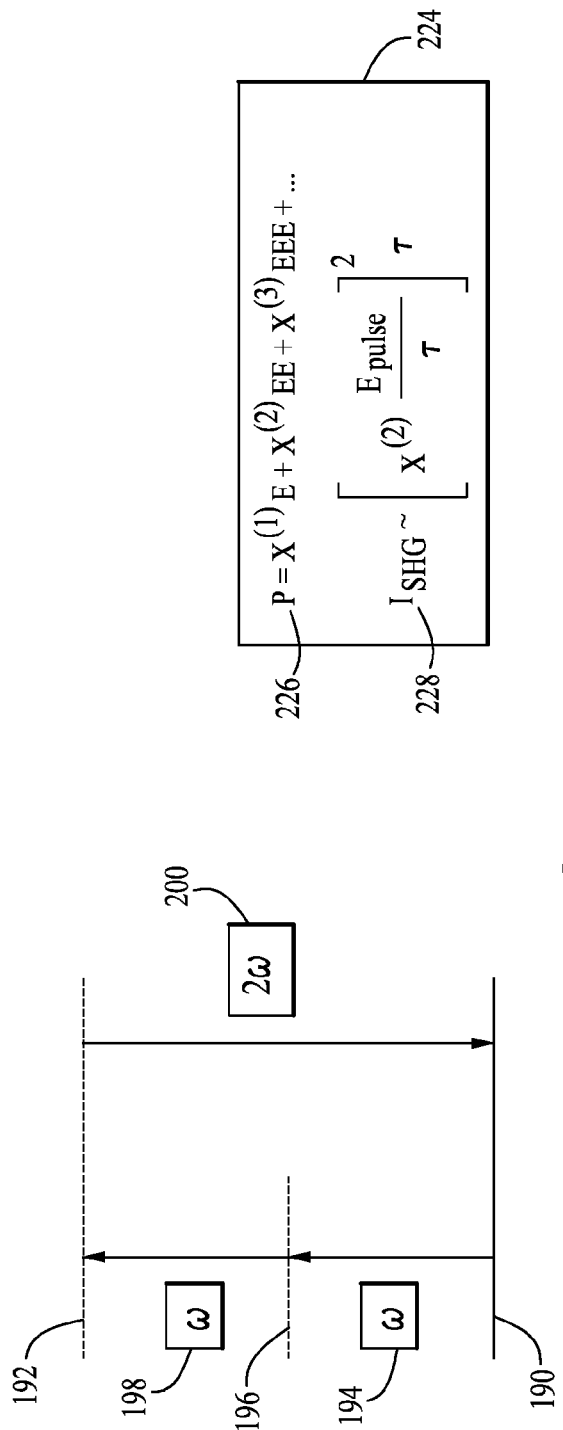
fig. 8

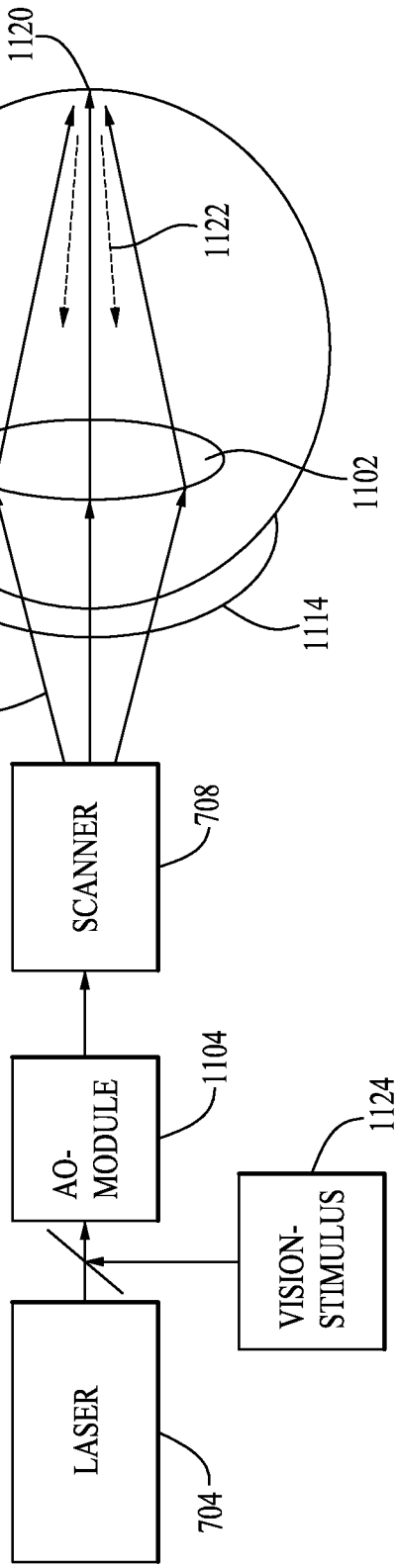

SYSTEM FOR CHARACTERIZING A CORNEA AND OBTAINING AN OPTHALMIC LENS

CROSS-REFERENCES

This application claims the benefit of the following U.S. provisional application Ser. Nos. 61/209,362 filed Mar. 4, 2009; 61/209,363 filed Mar. 4, 2009; 61/181,420 filed May 27, 2009; 61/181,519 filed May 27, 2009; and 61/181,525 filed May 27, 2009. These United States provisional applications are incorporated herein by reference. To the extent the following description is inconsistent with the disclosures of the provisional applications, the following description controls.

BACKGROUND

A variety of systems are known for characterizing a cornea, and using information from the characterization to model an ophthalmic lens. See for example U.S. Pat. Nos. 6,413,276; 6,511,180; 6,626,535; and 7,241,311

A difficulty with known systems for characterizing the cornea is that properties of the human cornea can be affected by the amount of water present at the time of measurement. Thus, for example, an ophthalmic lens designed for a patient, where the patient's cornea was characterized when the patient had a dry eye condition, may not be suitable for the patient when the patient's eye is adequately hydrated.

Another problem with conventional systems is the internal structure of the cornea usually is not considered. It is believed that the focusing effect of the cornea is achieved by the anterior surface of the cornea, the posterior surface of the cornea, and the interior structure of the cornea, each contributing about 80%, 10%, and 10%, respectively. This failure to consider the internal structure of the cornea, and in some instances failure to consider the shape of the posterior surface of the cornea, can result in a lens that provides unsatisfactory vision.

Accordingly, there is a need for an improved system for characterizing a cornea for the purpose of obtaining ophthalmic lenses for placement in the human eye. It is also desirable that the system permit analysis of effectiveness of a placed lens in focusing light on the retina.

The invention also includes a system for determining the clarity of vision of a patient to ascertain the effectiveness of an implanted lens or other ophthalmic modification provided to a patient. According to this method, the eye of the patient is illuminated with a scanning light of a wavelength that generates fluorescent light at the retina and clarity of the image generated by the fluorescent light is detected such as with a photodetector. Fluorescent light is generated by proteins in the pigment epithelial cells of the retina as well as photoreceptors of the retina. Then the path length of the scanning light is adjusted to increase the clarity of the image generated by the fluorescent light. Typically the scanning light has a wavelength of from 750 to about 800 nm, and preferably about 780 nm.

SUMMARY

The present invention provides a system that meets this need. The system includes a method and apparatus for determining the shape of the cornea of an eye, where the cornea has an anterior surface, a posterior surface, and an interior region between the anterior and posterior surfaces. The method relies upon generation of fluorescent light by the cornea, unlike prior art techniques, where reflectance of incident light is used for determining the cornea shape. According to the method, at least one of the anterior surface, the posterior surface and the interior region of the eye is illuminated with infrared light of a wavelength that can generate fluorescent light from the portion of the cornea illuminated. The generated fluorescent light is detected. The detected fluorescence can be used to generate a map of the anterior surface, posterior surface, and/or internal region of the cornea. By "anterior surface" there is meant a surface that faces outwardly in the eye. A "posterior surface" faces rearwardly toward the retina.

For example, in the case of the anterior region of the cornea, the optical path length at a plurality of locations in the interior region is determined. The presence of generated blue light from the interior region indicates the presence of collagen lamellae in the cornea.

Preferably the step of illuminating comprises focusing the infrared light in a plurality of different planes substantially perpendicular to the optical axis of the eye. The planes can intersect the anterior surface of cornea, the posterior surface of cornea, and/or the interior region of the cornea.

The present invention also includes apparatus for performing this method. A preferred apparatus comprises a laser for illuminating a selected portion of the cornea with infrared light of a wavelength that can generate fluorescent light from the portion of the cornea illuminated; focusing means such as focusing lenses for focusing the light in the selected portion of the cornea; and a detector, such as a photodiode detector, for detecting the generated fluorescent light.

The invention also includes a system for determining the clarity of vision of a patient to ascertain the effectiveness of an implanted lens or other ophthalmic modification provided to a patient. According to this method, the eye of the patient is illuminated with a scanning light of a wavelength that generates fluorescent light at the retina and the clarity of the image generated by the fluorescent light is detected such as with a photodetector. Fluorescent light is generated by proteins in the pigment epithelial cells as well as photoreceptors of the retina. Then the path length of the scanning light is adjusted to increase the clarity of the image generated by the fluorescent light. Typically the scanning light has a wavelength of from 750 to about 800 nm, and preferably about 780 nm. The term "clarity of vision" refers to the ability of a subject to distinguish two images differing in brightness (white is 100% bright and black is 0% bright). The less that the two images differ in contrast (relative brightness) where the subject can perceive the difference, the higher the subject's clarity of vision.

DRAWINGS

These and other features, aspects, and advantages of the present invention will become better understood with regard to the following description, appended claims, and accompanying drawings where:

Figure 7:
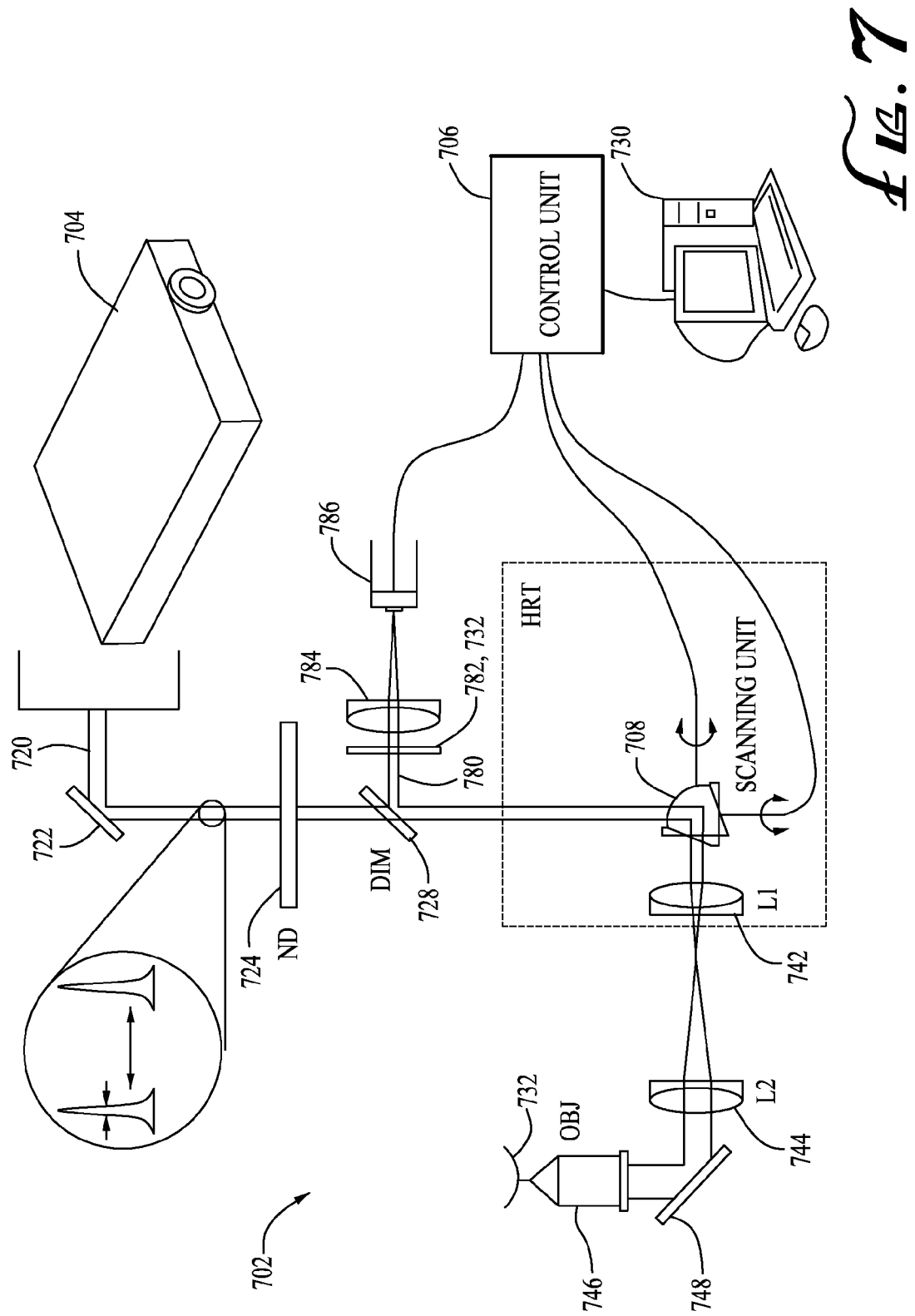
Figure 9:
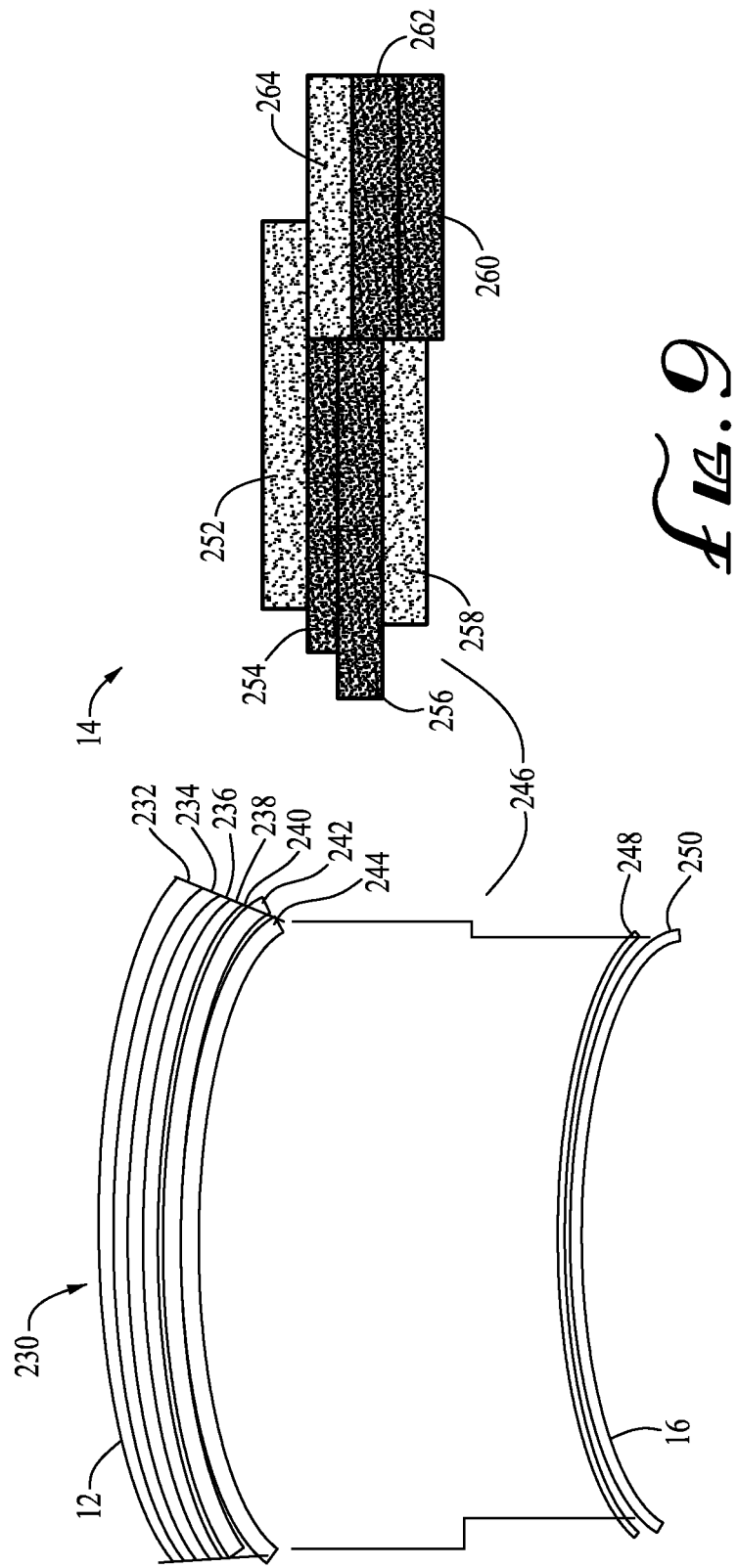
Figure 10:
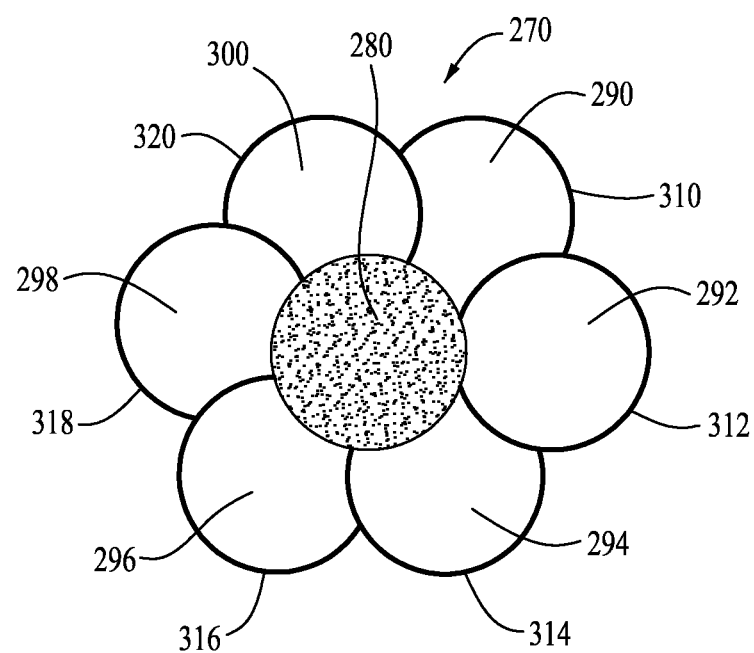

FIG. 7 schematically shows the major components of a two-photon microscope/opthalmoscope that can be employed in the present invention;

FIG. 8 is an overview of SHG-imaging of collagen tissue structures;

FIG. 9 sketches the micromorphometry of the cornea;

FIG. 10 shows a schematic arrangement for generating a composite cornea map over a field of view that resembles the size of a customized intraocular lens (C-IPSM); and FIG. 11 is a schematic view of a system for detecting the clarity of images achieved with an implanted intraocular lenses.

DESCRIPTION

Overview

A system for determining the topography of the cornea, including the topography of the anterior and posterior surfaces and interior regions of the cornea, includes measurement and simulation procedures that provide values for the refractive index distribution inside the cornea. Statistical distributions and results of finite element modeling of the stress/strain relationship inside the cornea can be employed.

The apparatus used can be a two-photon microscope to obtain a plurality of measurements with high spatial resolution. Each individual beam used in the apparatus can have a unique optical path length. The processes of Second Harmonic Generation imaging (SHGi) and Two Photon Excited Fluorescence imaging (TPEFi) are employed. By using a plurality of pixelized data that are generated from these measurements, a detailed spatial distribution of the refractive properties of the cornea can be evaluated for the purpose of fabricating an intraocular lens that can precisely compensate for detected aberrations.

The system also includes techniques for determining the effectiveness of a lens in the eye, i.e., a quality control technique.

Characterizing the Cornea

Figure 1:
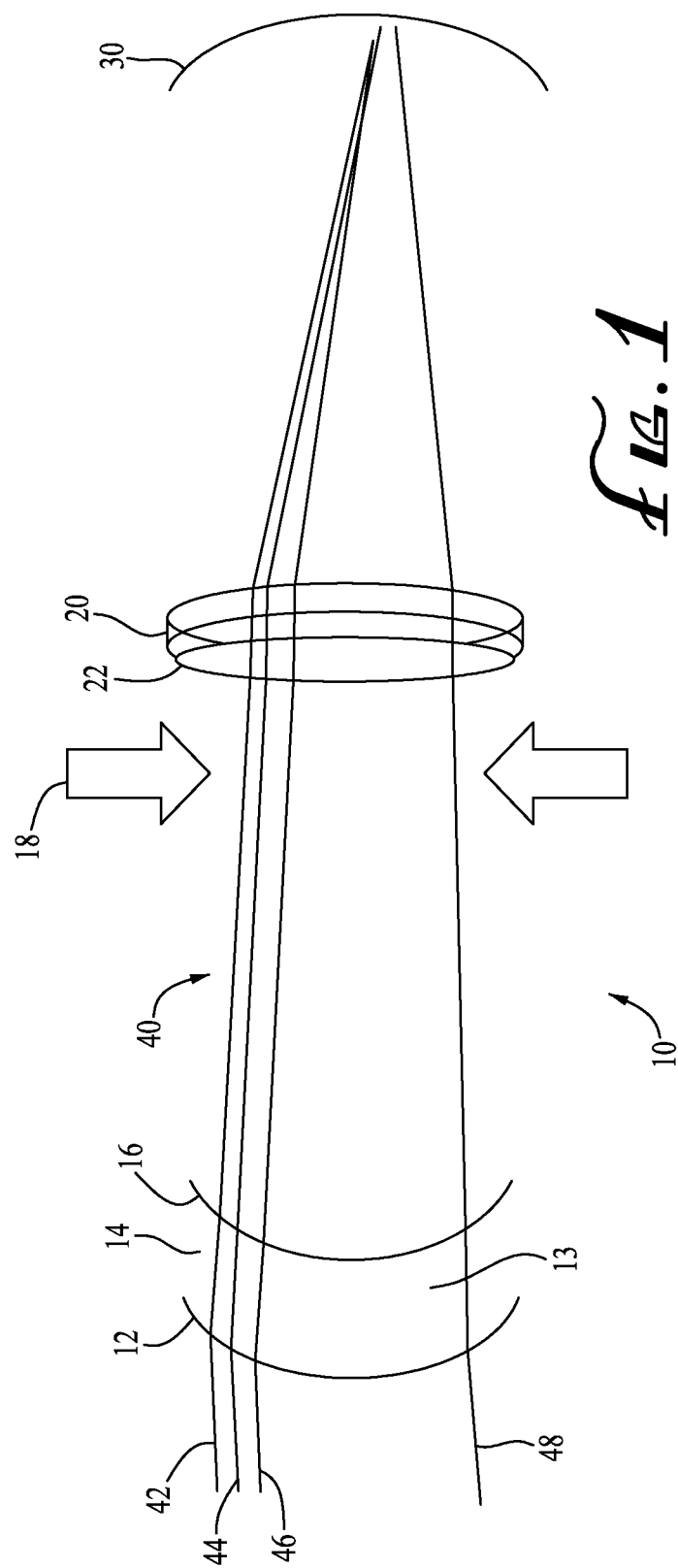
FIG. 1 is a schematic drawing of the method of the present invention being used with a pseudophakic eye.

Referring initially to FIG. 1, a system for determining the refractive properties of an implanted lens, such as a customized intraocular lens, is shown in a schematic drawing, and is generally designated 10. A plurality of optical rays 40 are transmitted through a pseudophakic eye, implanted with a customized intraocular lens 20, providing local corrections to the optical path lengths of the individual optical rays with high spatial resolution. These optical rays are directed through the pseudophakic eye to form an image on the retina 30. The plurality of individual beams 40 are characterized by the fact that each beam has a unique optical path length. Specifically, each optical path length is indicative of the refraction that was experienced by its respective individual beam during transit of the individual beam through the eye. Next, the optical path lengths of the individual beams are collectively used by a computer to create a digitized image on the retina of the eye. The plurality of optical rays 40 is transmitted in sequence through the anterior surface 12 of the cornea 14, the interior region 13 of the cornea 14, the posterior surface 16 of the cornea 14, and a customized intraocular lens, having an anterior surface layer 22, and is brought to a focused image on the retina 30. A method for forming the lens 20 is described in my co-pending application Ser. No. 12/717,886, filed on Mar. 4, 2010, entitled "System for Forming and Modifying Lenses and Lenses Formed Thereby", which is incorporated herein by reference.

In the upper part of the plurality of optical rays 40, three neighboring rays 42, 44, and 46 are depicted, symbolizing a local zone in the zonal approach. Typically, in ray tracing calculations of highest spatial resolution, tens of millions of rays are evaluated with regard to their optical path lengths in the human eye. For calculation purposes, a reference plane 18, close to the natural pupil of the pseudophakic eye, is selected, towards which the optical path lengths of the individual beams are normalized. In particular, the propagation of an individual optical ray from the pupil plane 18 to the anterior surface 22 of the customized intraocular lens 20 can be evaluated as $\exp(i \times (2\pi/\lambda) \times n(x,y) \times z(x,y))$, where exp resembles the exponential function, i denotes the imaginary unit number, $\pi$ amounts to approximately 3.14, $\lambda$ denotes the wavelength of the optical ray, $n(x,y)$ describes the local refractive index and $z(x,y)$ the physical distance at the transverse location with coordinates x and y from the pupil plane 18. Any inaccuracy of the positioning of the customized intraocular lens (C-IPSM) 20 during lens implantation with regard to axial or lateral position or tilt can be expressed by a profile of physical lengths $z(x,y)$ and can be compensated for by in-vivo fine-tuning of the surface layer 22 with an optical technique, as described in my aforementioned copending application Ser. No. 12/717,886, filed on Mar. 4, 2010, entitled "System for Forming and Modifying Lenses and Lenses Formed Thereby," which is incorporated herein by reference.

Figure 2:
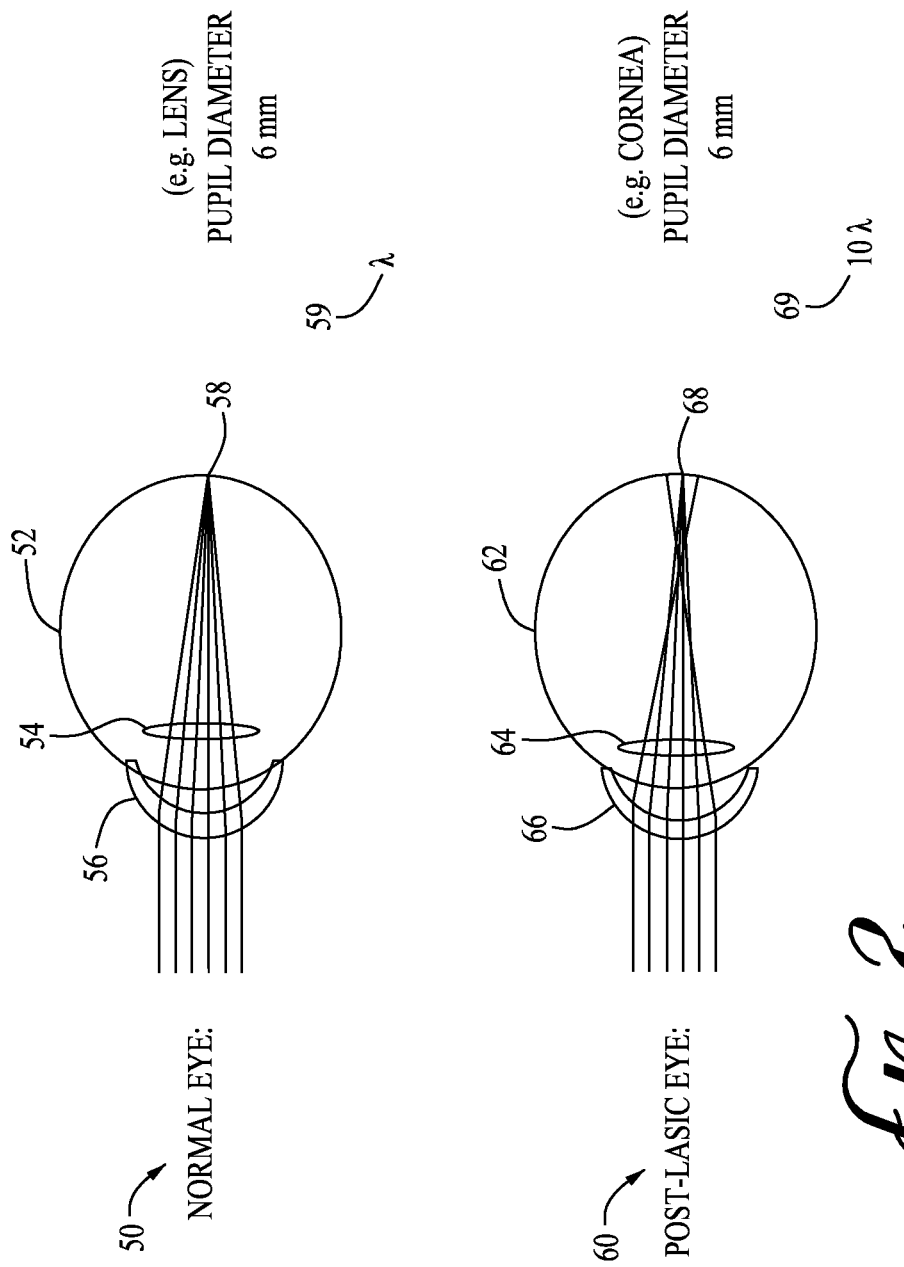
FIG. 2 is a graphical presentation of the presence of spherical aberration of the crystalline lens of the human eye, and in a post-LASIK eye.

FIG. 2 is a graphical presentation of the presence of one particular optical aberration of the human eye, e.g. spherical aberration, in a normal eye (e.g. crystalline lens) and in a post-LASIK eye (e.g. reshaped cornea), visualizing the induction of spherical aberration in a post-LASIK eye 60. In the upper part of FIG. 2, the situation in a normal eye 50 is exemplified. The eyeball 52 contains a cornea 56, a lens 54 and a retina 58. Typically, for a pupil diameter of 6 mm, an amount of spherical aberration 59 of approximately one wavelength $\lambda$, corresponding to 0.5 μm, is introduced, mainly associated with the peripheral shape of the crystalline lens. In the lower part of FIG. 2, for the case of a post-LASIK eye 60, which underwent a myopia correction procedure, the introduction of a considerable amount of spherical aberration is demonstrated. The eyeball 62 exhibits a cornea 66, a lens 64 and a retina 68. Typically, an amount of spherical aberration of approximately ten wavelengths ($10\lambda$), corresponding to 5 is encountered, mainly associated with the edges of the centrally flattened cornea.

Figure 3:
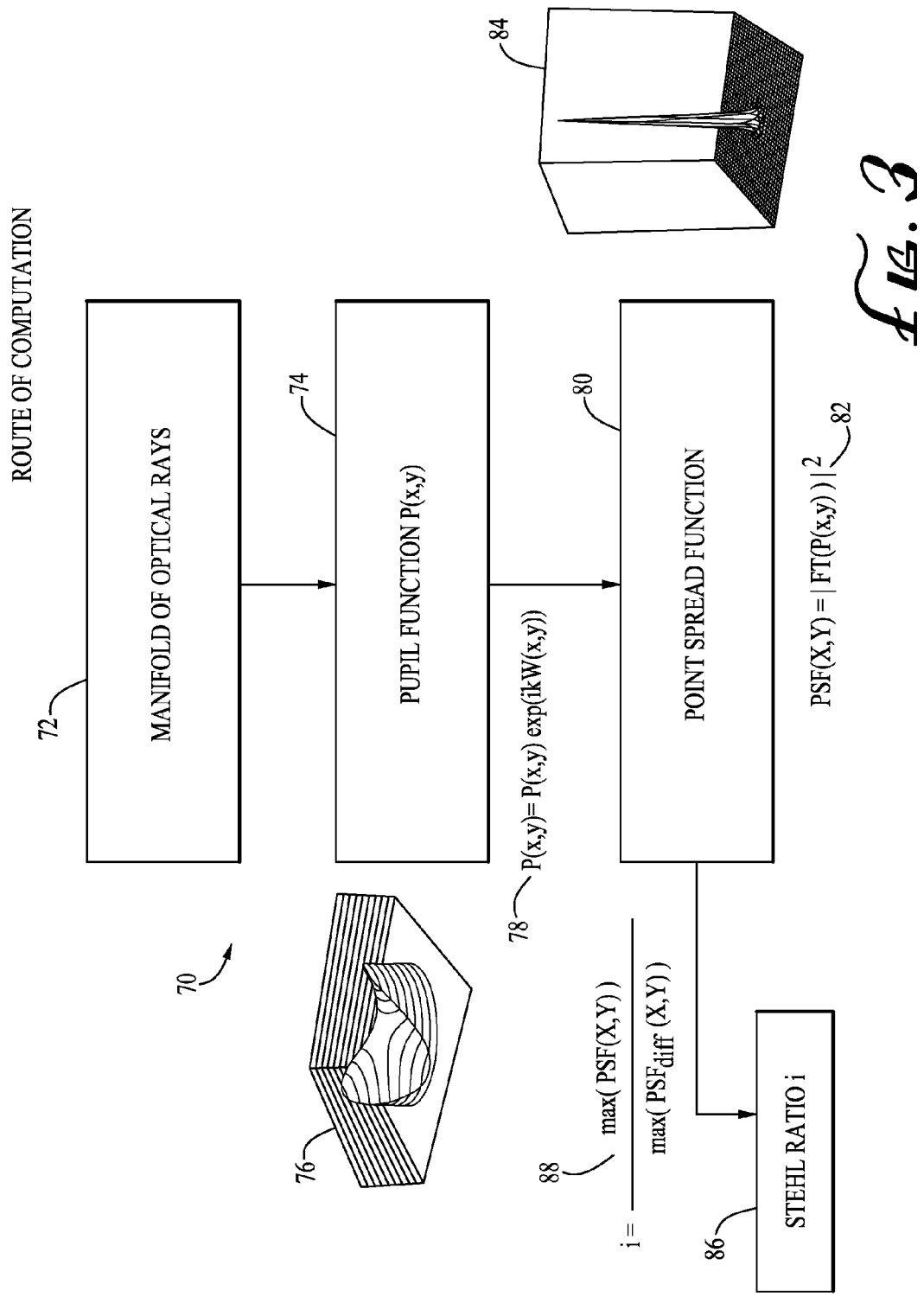
FIG. 3 is a schematic presentation of a route of calculation to determine clarity of a retinal image.

FIG. 3 is a schematic presentation of a route of calculation 70 for determining the necessary refractive effect of an implanted lens. A manifold of optical rays 72 is transformed into a pupil function 74 which can be visualized as the spatial distribution of the path lengths 76 and can be expressed as the mathematical function 78: $P(x,y)=P(x,y) \exp(ikW(x,y))$, where $P(x,y)$ is the amplitude and $\exp(ikW(x,y))$ is the phase of the complex pupil function. The phase depends on the wave vector $k=2\pi/\lambda$, $\lambda$ being the wavelength of the individual optical ray, $W(x,y)$ being its path length, and i denotes the imaginary unit number. From the pupil function 74 the point spread function (PSF) 80 can be derived which mathematically can be expressed as a Fourier Transform 82: $PSF(x,y)=|FT(P(x,y))|^2$, which is graphically represented as a pseudo-three dimensional function 84, depicting a nearly diffraction-limited case, exhibiting a pseudophakic eye with only minor optical aberrations. From the calculation 70, the Strehl Ratio i 86 can be derived which is defined as 88: $i=(\max(PSF(x,y))/$ max(PSF$_{diff}$(x,y)), where PSF(x,y) denotes the point spread function of the aberrated optical system, and PSF$_{diff}$(x,y) resembles an idealized diffraction-limited optical system. The point spread function (PSF) 80 and the Strehl Ratio i 86 are useful to visualize the optical quality of an eye and the clarity of a retinal image.

Figure 4:
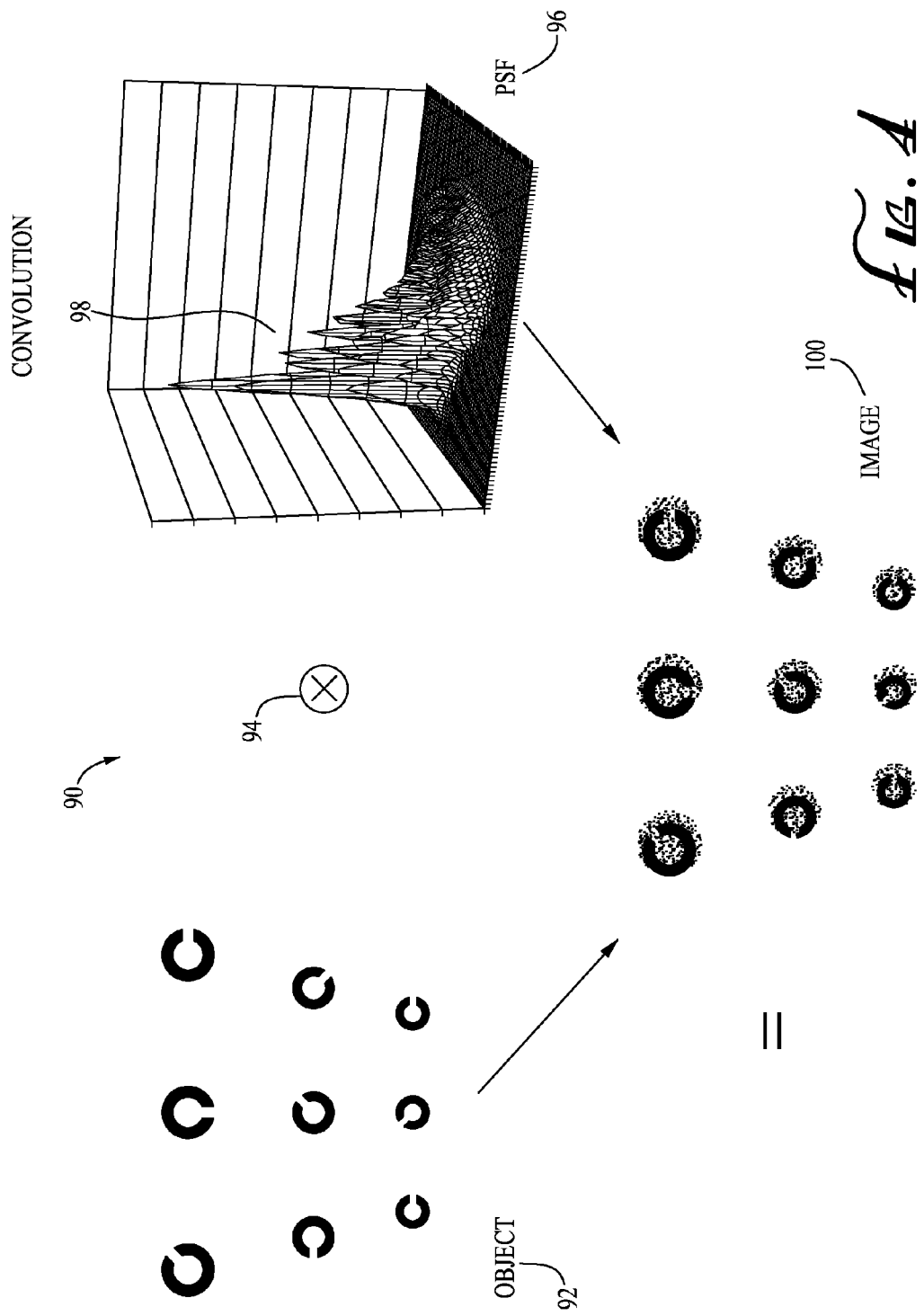
FIG. 4 is a graphical visualization of the mathematical procedure of convolution which can be employed in a computing method to determine clarity of vision.

FIG. 4 is a graphical visualization of the mathematical procedure of convolution which can be employed for the purpose of evaluating the clarity of the retinal image. The image formation process 90 can be envisaged as a mathematical operation—called convolution 94—in which the idealized image of an object 92 is blurred by convolving each image point with the point spread function PSF 96 of the optical system resulting in an image 100. For the ease of a human eye with a pupil of 6 mm diameter, the PSF 96 is depicted as a pseudo-three dimensional graph 98. Thus, the clarity of the retinal image 100 can be ascertained by the point spread function PSF 96.

Figure 5:
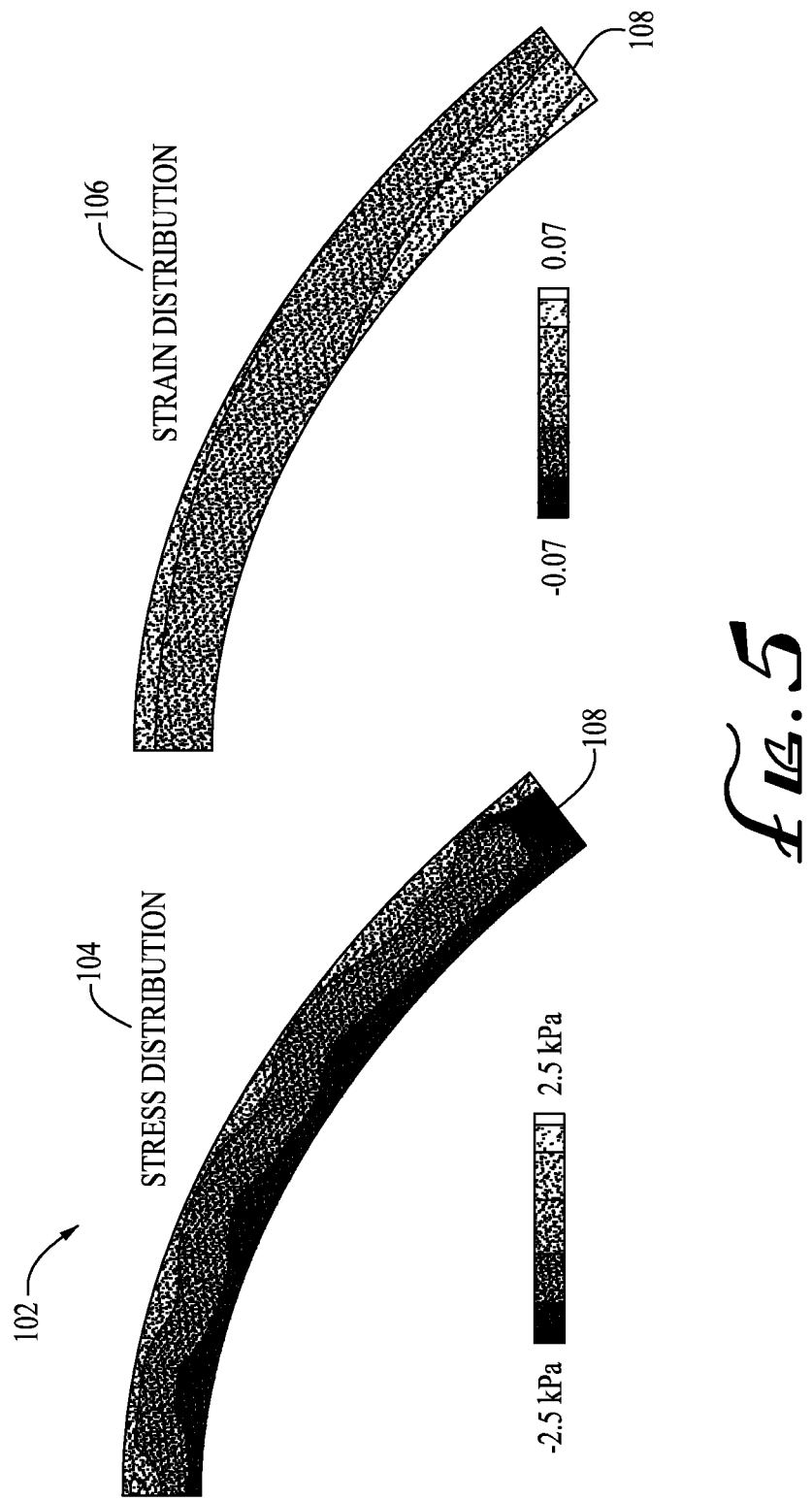
FIG. 5 is a side cross sectional view showing the stress strain distribution in a loaded cornea as the result of Finite Element Modeling (FEM)

FIG. 5 is a side cross-sectional view showing the stress and strain distribution in a loaded cornea as the result of Finite Element Modeling (FEM). By employing a Finite Element Modeling (FEM) algorithm 102 for simulating the stress 104 and strain 106 distribution throughout a loaded cornea, the local density of the stromal tissue inside the cornea can be determined, from which the spatial distribution of the refractive index n (x,y) is derived, yielding a measure of the variability of the optical path lengths of the manifold of the optical rays inside the cornea. Initially, finite element Modeling (FEM) provides the distribution of stiffness parameters in the volume elements, which are proportional to local tissue densities. The application of FEM-modeling to cornea biomechanics is described in, e.g., A. Pandolfi, et al., Biomechan. Model Mechanobiology 5237-246, 2006. An intraocular pressure of 2 kiloPascal (kPA) (15 mm Hg) is applied homogeneously to the posterior surface. Only Bowman's layer 108 is fully fixed at the limbus. On the left part of FIG. 5, a Cauchy stress distribution along the radial direction is depicted; the absolute values range from −2.5 kPa to +2.5 kPa. On the right part of FIG. 5, the maximum principle strain distribution is visualized; the relative compression resp. dilation of the stromal tissue range from −0.07 to +0.07.

Use of Fluorescent Emission to Characterize a Cornea

Figure 6:
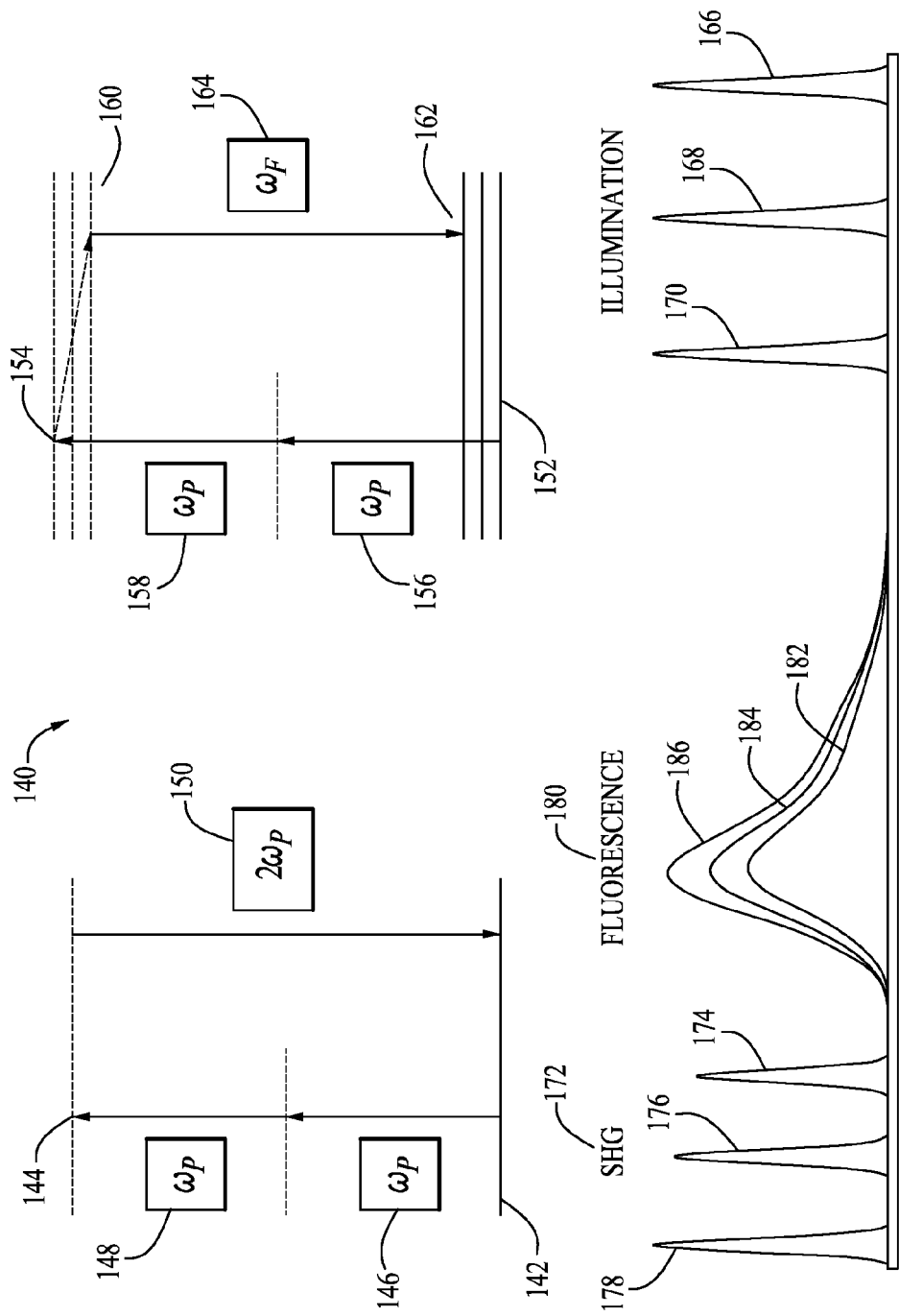
FIG. 6 is a schematic drawing depicting the physical processes of second harmonic generation imaging (SHGi) and two photon excited fluorescence imaging (TPEFi)

FIG. 6 is a schematic drawing depicting the physical processes of second harmonic generation imaging (SHGi) and two photon excited fluorescence imaging (TPEFi). On the upper left side of FIG. 6, the principle of Second Harmonic Generation imaging (SHGi) 140 is shown. Two photons 146 and 148 with frequency $\omega_p$ coherently add on to generate a photon 150 with frequency $2\omega_p$ which is instantaneously reradiated from level 144 to 142. In the upper right side of FIG. 6, the Two Photon Excited Fluorescence imaging (TPEFi) process is visualized. Two photons 156 and 158 with frequency $\omega_p$ excite a molecule from the ground level 152 to an excited level 154. After thermal relaxation to level 160 in about 1 picosecond, the fluorescence photon $\omega_F$ is reradiated, as the molecule is de-excited to level 162 in about 1 nanosecond. In the lower part of FIG. 6, the wavelength dependence of the SHGi (Second Harmonic Generation)- and TPEFi (Two Photon Excited Fluorescence)-imaging processes are exemplified. Generally, as the wavelength of the illuminating femtosecond laser beam with frequency $\omega_p$ is decreased from 166 via 168 to 170, the intensity of the SHGi-signals 174, 176 and 178 with frequency $2\omega_p$ are increased, as well as the intensities of the TPEFi signals 182, 184 and 186 with frequency $\omega_F$. In the Two Photon Cornea Microscope/Opthalmoscope, as described with regard to FIG. 7, a wavelength of 780 nm of the illuminating femtosecond laser is used, for optimized contrast of the imaging of collagen fibrils and cell processes inside the cornea.

FIG. 7 schematically shows a preferred apparatus 702 for characterizing a cornea for designing a customized intraocular lens. The apparatus 702 comprises a laser 704, preferably a two-photon laser, a control unit 706, and a scanning unit 708. Two-photon excitation microscopy is a fluorescence imaging technique that allows imaging living tissue up to a depth of one millimeter. The two-photon excitation microscope is a special variant of the multiphoton fluorescence microscope. Two-photon excitation can be a superior alternative to confocal microscopy due to its deeper tissue penetration, efficient light detection and reduced phototoxicity. The concept of two-photon excitation is based on the idea that two photons of low energy can excite a fluorophore in a quantum event, resulting in the emission of a fluorescence photon, typically at a higher energy than either of the two excitatory photons. The probability of the near-simultaneous absorption of two photons is extremely low. Therefore, a high flux of excitation photons is typically required, usually a femtosecond laser.

A suitable laser is available from Calmar Laser, Inc., Sunnyvale, Calif. Each pulse emitted by the laser can have a duration of from about 50 to about 100 femtoseconds and an energy level of at least about 0.2 nJ. Preferably the laser 704 generates about 50 million pulses per second at a wavelength of 780 nm, a pulse length of about 50 fs, each pulse having a pulse energy of about 10 nJ, the laser being a 500 mW laser. An emitted laser beam 720 is directed by a turning mirror 722 through a neutral density filter 724 to select the pulse energy. The laser beam 720 typically has a diameter of about 2 mm when emitted by the laser. The laser beam 720 then travels through a dichroic mirror 728 and then to the scanning unit 708 that spatially distribute the pulses into a manifold of beams. The scanning unit 708 is controlled by a computer control system 730 to scan a cornea 732 in an eye.

The beam 720 emitted from the laser has a diameter from about 2 to about 2.5 mm. The beam 720, after exiting the scanner 708, is then focused by focusing means to a size suitable for scanning the cornea 732, typically a beam having a diameter from about 1 to about 2 μm. The focusing means can be any series of lenses and optical devices, such as prisms, that can be used for reducing the laser beam to a desired size. The focusing means can be a telescopic lens pair 742 and 744 and a microscope objective 746, where a second turning mirror 748 directs the beam from the lens pair to the microscopic objective. The focusing microscope objective can be a 40×/0.8 objective with a working distance of 3.3 mm. The scanning and control unit are preferably a Heidelberg Spectralis HRA scanning unit available from Heidelberg Engineering located in Heidelberg, Germany.

The optics in the scanning unit allow a region having a diameter of about 150 to about 450 μm to be scanned without having to move either the cornea 732 or the optics. To scan other regions of the cornea it is necessary to move the cornea in the x-, y-plane. Also, to scan in varying depths in the cornea, it is necessary to move the focal plane of the laser scanner in the z-direction.

The control unit 706 can be any computer that includes storage memory, a processor, a display, and input means such as a mouse, and/or keyboard. The control unit is programmed to provide a desired pattern of laser beams from the scanning unit 708.

The cells on the anterior surface of the cornea 732, when excited by the laser beam at a wavelength of 780 nm fluoresce, producing a green light having a wavelength of about 530 nm.

The emitted light tracks through the path of the incident laser light, namely the emitted light passes through the microscope objective 746, to be reflected by the turning mirror 748, through the lenses 744 and 742, through the scanning unit 708 into the dichroic mirror 728 which reflects the fluorescent light to path 780, generally at a right angle to the path of the incident laser light that passed through the dichroic mirror 728. In path 780, the emitted light passes through a filter 782 to remove light of unwanted frequencies, and then through a focusing lens 784 to a photodetector 786. The photodetector can be an avalanche photodiode. Data from the photodetector can be stored in the memory of the computer control unit 730, or in other memory.

Thus, the anterior surface of the cornea is illuminated with infrared light of a wavelength that generates fluorescent light and the generated fluorescent light is detected. For the anterior surface, incident infrared light is focused in a plurality of different planes that are substantially perpendicular to the optical axis of the eye, where the planes intersect the anterior surface of the cornea.

The same procedure can be used for characterizing the posterior surface, by focusing the infrared light in a plurality of different planes substantially perpendicular to the optical axis of the eye where the planes intersect the posterior surface. The scanning can be done in 64 separate planes, where the scanning is done with beams about three microns apart.

A difference for scanning the interior of the cornea is that the collagen lamellae in the interior region generate blue light rather than green light. The blue light has a wavelength of about 390 nm. When scanning the interior of the cornea, it is necessary to use a different filter 732 to be certain to have the blue light pass through the filter to the photodetector 786.

FIG. 8 is an overview of SHG-imaging of collagen tissue structures. The collagen triple helix 188 is visualized in the upper left part of FIG. 8, exhibiting the typical structure of collagen fibrils. The collagen fibrils are organized in a complex three dimensional layered structure inside the corneal stroma. On the lower left part of FIG. 8, the Second Harmonic Generation (SHG) laser/collagen fibril interaction process is depicted. A photon 194 with the frequency ω polarizes the collagen fibril to an intermediate level 196, whereas a second photon 198 of the same frequency ω further creates an instantaneous electronic level 192. The electronic excitation is immediately reradiated as a photon 200 of double energy, exhibiting the frequency 2ω. This process occurs with high yield because of the unidirectional shape of the collagen fibrils. Second Harmonic Generation imaging (SHGi) of corneal tissue was recently reported (M.Han, G. Giese, and J. F. Bille, "Second harmonic generation imaging of collagen fibrils in cornea and sclera", Opt. Express 13, 5791-5795 (2005)). The measurement was performed with the apparatus of FIG. 7. The SHGi signal is determined according to the formulas 224 from the nonlinear optical polarization 226 of the collagen fibrils. The signal-strength 228 is directly proportional to the second order polarization term $[\chi^{(2)}]^2$ and inversely proportional to the pulse length T of the femtosecond laser pulses. Thus, a SHGi-image of high contrast visualizes the three dimensional layered structure of the corneal stroma, due to the strong unidirectionality of the collagen fibrils and the ultrashort pulse length of the femtosecond laser employed in the in-vivo Two Photon Cornea Microscope/Opthalmoscope, as described with regard to FIG. 7.

Anatomically, the cornea 14 of an eye is shown in FIG. 9 to include, in order from its anterior surface 12 to its posterior surface 16, an epithelium 230, a Bowman's membrane 244, a stroma 246, a Descemet's membrane 248, and an endothelium 250. The epithelium 230 is comprised of several cell layers, e.g. 232, 234, 236, 238 and 240, merging into the basal cell layer 242. The basal cell layer 242, as well as the anterior surface 12, can clearly be imaged by the two-photon excited autofluorescence mode (TPEF) of the two-photon cornea microscope, providing a spatially resolved measure of the thickness of the epithelium 230. The endothelium can also be imaged by the two-photon excited autofluorescence mode of the two-photon cornea microscope, resulting in a spatially resolved thickness measurement of the cornea 14. The stroma 246 is composed of approximately 200 collagen lamellae, e.g. 252, 254, 256, 258, 260, 262, and 264, exhibiting a complex three dimensional structure, which can be evaluated utilizing the Second Harmonic Generation imaging (SHGi) mode of the two-photon cornea microscope. Based on these measurements, supported by Finite Element Modeling (FEM) of the stiffness of the collagen structure—as exemplified in FIG. 5—the three-dimensional distribution of the refractive index inside the cornea can be reconstructed. Thus, the optical path lengths—inside the cornea—of the plurality of the optical rays in the ray-tracing calculation can be determined with high spatial resolution. Thus the anterior surface, posterior surface and/or internal structure of the cornea can be mapped.

In FIG. 10, the formation of a composite cornea map 270 from individual imaging fields is demonstrated. Typically, a central imaging field 280 extends over a diameter of about 2 mm, comprising approximately 2000×2000 imaging pixels, which amount to 4 million imaging points or pixels, providing a resolution of approximately 1 μm (e.g. utilizing a Nikon 50×/0.45 microscope objective.). The composite cornea map 270 contains a three dimensional stack of two-photon microscope images, comprised of either the Two-Photon Excited Fluorescence imaging (TPEFi)- or the Second Harmonic Generation imaging (SHGi)-imaging mode. In order to match the size of the customized intraocular lens of approximately 6 mm diameter, six peripheral imaging fields 290, 292, 294, 296, 298, and 300 are employed. The alignment of the individual fields is accomplished by utilizing a run-time grey value pixel cross correlation algorithm in the overlap zones 310, 312, 314, 316, 318, and 320. Thus, the composite cornea map exhibits approximately 28 million data, providing a spatially resolved composite image of one transversal slice through the cornea. Typically, one hundred transversal slices through the cornea are employed for reconstructing the optical path lengths of the plurality of optical rays as they are transmitted through the cornea of the pseudophakic eye.

Designing and Forming Lenses

Techniques for designing lenses from the data generated by the apparatus of FIG. 7 are known in the art and include the methods described by Roffman in U.S. Pat. No. 5,050,981, which is incorporated herein by reference with regard to such methods. Techniques for manufacturing or modifying a lens are described in my aforementioned copending U.S. patent application Ser. No. 12/717,886.

Clarity of Vision Determination

With regard to FIG. 11 there is schematically shown a system for determining the clarity of vision experienced by a patient, and in the instance of FIG. 11, with an implanted intraocular lens 1102. The system used for this is substantially the same as the apparatus shown in FIG. 7 using the same laser 704 and scanner 708. Optionally an adaptive-optics module (AO-module) 1104 can be used for the purpose of simulating the effect of a refractive correction, with regard to image clarity and depth of focus. The AO-module 708 can be composed of a phase-plate compensator and an active mirror for the purpose of pre-compensating individual light beams generated by the laser 704. An adapted optics device to compensate for asymmetric aberrations in a beam of light useful for the invention described in my U.S. Pat. No. 7,611,244. A method and apparatus for pre-compensating the refractive properties of the human with an adaptive optical feedback control is described in my U.S. Pat. No. 6,155,684. Use of active mirrors is described in my U.S. Pat. No. 6,220,707. Individual light beams 1112 pass through the cornea 1114 and then the intraocular lens 1102 to be focused on the retina to form a retinal image at 1120. With the incoming light being at a wavelength of from about 750 to about 800 nm, preferably about 780 nm, fluorescent proteins in the pigment epithelial cells, as well as the photoreceptors, emit fluorescent light having a frequency of about 530 nm to about 550 nm. The emitted light is represented by lines 1122 in FIG. 11. The intensity of the fluorescent light emitted indicates and correlates with how well the cornea 1114 and intraocular lens 1102 focus the incoming light beams, wherein higher intensity indicates better focusing. To determine if improved focusing can be obtained, to increase the clarity of the image generated by the fluorescent light, the path length of the incoming scanning light can be changed, such as by adjusting the phase plate or the active mirror in the adaptive optics module 1104.

Optionally, vision stimulae 1124, such as a Snellen chart can be provided, to receive subjective feedback from the patient with regard to the clarity of vision.

Using the method, a prescription for an implanted lens, such as an IOL, corneal lens, or contact lens, as well as modification for an in situ lens (cornea, IOL, natural crystalline lens) can be determined.

Although the present invention has been described in considerable detail with reference to the preferred versions thereof, other versions are possible. For example, although the present invention is described with regard to use of intraocular lenses, it is understood that the data generated characterizing the cornea can be used for forming contact lenses and other lenses implanted in an eye. Therefore the scope of the appended claims should not be limited to the description of the preferred versions contained therein.

What is claimed is:

1. A method for generating a map of a cornea of an eye, the cornea having an anterior surface, a posterior surface, and an interior region between the anterior and posterior surfaces, the method comprising the steps of:
    a) illuminating a portion of the cornea by scanning focused infrared light in a plurality of different planes within said portion of the cornea that are substantially perpendicular to an optical axis of the eye, said plurality of planes intersecting the following:
        i) a first portion of the anterior surface and a first portion of the posterior surface; and
        ii) a second portion of the anterior surface, a second portion of the interior region and a first portion of the posterior surface, and
        iii) a second portion of the posterior surface and a third portion of the interior region,
    wherein the infrared light is of a wavelength that generates fluorescent light and a Second Harmonic Generation imaging (SHGi) signal by nonlinear optical processes from the portion of the cornea illuminated;
    b) detecting and evaluating the fluorescent light and SHGi signal generated from the portion of the cornea illuminated;
    c) determining the shape of the anterior and posterior surfaces and a spatially resolved thickness measurement of the portion of the cornea illuminated from the detected fluorescent light and the SHGi signal;
    d) determining from the SHGi signal the three dimensional layered structure of stroma tissue;
    (e) deriving, using finite element modeling, optical path lengths for the portion of the cornea illuminated from the detected fluorescent light and SHGi signal;
    (f) using the derived optical path lengths to generate a map of the anterior surface, posterior surface and the interior region for the portion of the cornea illuminated.

2. The method of claim 1 wherein the nonlinear optical processes comprise a Two Photon Excited Fluorescence imaging (TPEFi) process and the detecting and evaluating step comprises detecting any generated green light, wherein the presence of green light indicates the anterior or posterior surfaces of the cornea.

3. The method of claim 2 wherein the green light has a wavelength of about 530 nanometers.

4. The method of claim 1 wherein the nonlinear optical processes comprise a Second Harmonic Generation imaging (SHGi) process and the detecting and evaluating step comprises detecting any generated blue light, wherein the presence of blue light indicates the presence of collagen lamellae in the cornea.

5. The method of claim 4 wherein the blue light has a wavelength of about 390 nanometers.

6. The method of claim 1 wherein, step f) further includes determining a three dimensional distribution of refractive index in the portion of the cornea illuminated from the derived optical path lengths in the portion of the cornea illuminated.

7. The method of claim 1 wherein the wavelength of the infrared light is about 780 nm.

8. The method of claim 1 wherein the infrared light is emitted as pulses having an energy level of at least 0.2 nJ.

9. The method of claim 1 wherein the wavelength of the infrared light is about 750-800 nm.

* * * * *